(12) United States Patent  
Giraudet (10) Patent No.: US 8,783,872 B2  
(45) Date of Patent: Jul. 22, 2014

(54) METHOD FOR PROVIDING A SPECTACLE OPHTHALMIC LENS BY CALCULATING OR SELECTING A DESIGN

(75) Inventor: Guillaume Giraudet, Charenton-Le-Pont (FR)

(73) Assignee: Essilor International (Compagnie Generale d'Optique), Charenton le Pont (FR)

(*) Notice: Subject to any disclaimer, the term of this patent is extended or adjusted under 35 U.S.C. 154(b) by 323 days.

(21) Appl. No.: 13/142,381

(22) PCT Filed: Dec. 24, 2009

(86) PCT No.: PCT/EP2009/067921  
§ 371 (c)(1), (2), (4) Date: Sep. 28, 2011

(87) PCT Pub. No.: WO2010/072840  
PCT Pub. Date: Jul. 1, 2010

(65) Prior Publication Data  
US 2012/0019776 A1    Jan. 26, 2012

(30) Foreign Application Priority Data  
Dec. 26, 2008 (EP) ..................................... 08306023

(51) Int. Cl.  
*A61B 3/00* (2006.01)  
*A61B 3/10* (2006.01)  
*G02C 13/00* (2006.01)

(52) U.S. Cl.  
CPC ................................ *A61B 3/1015* (2013.01)  
USPC ........................... 351/246; 351/204; 351/178

(58) Field of Classification Search  
USPC .................................. 351/204, 177, 246, 178  
See application file for complete search history.

(56) References Cited

U.S. PATENT DOCUMENTS 6,932,090 B1    8/2005   Reschke et al.

FOREIGN PATENT DOCUMENTS

| EP | 0 940 117 | 9/1999 |
| EP | 1 747 750 | 1/2007 |
| EP | 1 830 223 | 9/2007 |
| FR | 2 912 820 | 8/2008 |

*Primary Examiner* — Jack Dinh  
(74) *Attorney, Agent, or Firm* — Cozen O'Connor (57) ABSTRACT

A method for providing a spectacle ophthalmic lens to a wearer, the method comprising the following steps: providing a value, SV, representing the sensitivity of the wearer referred to a scale of sensitivity to perception of spatial orientation, according to both visual and non visual frames of reference; calculating a design of the spectacle ophthalmic lens or selecting a design in a spectacle ophthalmic lens design data base by adapting the management of residual astigmatism and/or optical power repartition according to gaze direction based on the value, SV, representing the sensitivity of the wearer referred to a scale of sensitivity to perception of spatial orientation.

14 Claims, 9 Drawing Sheets

FIG. 8

METHOD FOR PROVIDING A SPECTACLE OPHTHALMIC LENS BY CALCULATING OR SELECTING A DESIGN

RELATED APPLICATIONS

This is a U.S. National Phase Application under 35 USC 371 of International Application PCT/EP2009/067921 filed on Dec. 24, 2009.

This Application claims the priority of European Application No. 08306023.6 filed Dec. 26, 2008, the entire content of which is hereby incorporated by reference.

FIELD OF THE INVENTION

The invention relates generally to the field of vision improvement and more specifically concerns a method for providing an spectacle ophthalmic lens by calculating or selecting a design. The spectacle ophthalmic lens can be, e.g., a progressive lens, a unifocal lens. The invention also concerns a method for making a spectacle ophthalmic lens. Furthermore, the invention concerns a piece of software set up for implementing the calculation method for the design of a spectacle ophthalmic lens of the invention.

BACKGROUND OF THE INVENTION

Spectacle ophthalmic lenses are worn and widely used for correcting many different types of vision deficiencies. These include defects such as near-sightedness (myopia) and far-sightedness (hypermetropia), astigmatism, and defects in near-range vision usually associated with aging (presbyopia).

Ophthalmologists or optometrists routinely improve the visual acuity by correcting refractive errors of an eye in terms of sphere, cylinder and axis.

Astigmatism of an eye occurs when the refractive error in an eye is meridian-dependent. This is usually due to one or more refractive surfaces, most commonly the anterior cornea, having a toroidal shape.

SUMMARY OF THE INVENTION

One object of the invention is to better meet the visual needs of lens users and improve the comfort of lens users, particularly users of progressive lens, and facilitate their adapting to the lenses.

For this purpose, one aspect of the invention is directed to a method implemented by computer means for providing a spectacle ophthalmic lens to a wearer, the method comprising the following steps:
  providing a value, SV, representing the sensitivity of the wearer referred to a scale of sensitivity to perception of spatial orientation, according to both visual and non visual frames of reference;
  calculating a design of the spectacle ophthalmic lens or selecting a design in a spectacle ophthalmic lens design data base by adapting the management of residual astigmatism and/or optical power repartition according to gaze direction based on the value, SV, representing the sensitivity of the wearer referred to a scale of sensitivity to perception of spatial orientation.

Humans typically stand with postural orientation that is near to upright with respect to the direction of gravity. The nervous system combines different types of sensory information to establish a reference, for this preferred postural orientation. The nervous system has access to multiple sources of sensory information about the relative alignment of the body segments to each other and to the environment, including visual, somatosensory, including proprioceptive, tactile, and joint, vestibular and truncal graviceptor information. However, to establish and maintain a set point for postural orientation, this multimodal sensory information must be integrated and interpreted with respect to a stable frame of reference that is relevant to the postural task.

Examples of frames of reference are disclosed in following documents:

Gibson J J (1952) "*The relation between visual and postural determinants of the phenomenal vertical*" Psychol Rev 59:370-375;

Stoffregen T A, Riccio G E (1988) "*An ecological theory of orientation and the vestibular system*" Psychol Rev 95:3-14;

Berthoz A (1991) "*Reference frames for the perception and control of movement*" In: Paillard J (ed) Brain and space. Oxford University Press, Oxford, pp 81-111;

Mittelstaedt H (1996) "*Somatic graviception*" Biol Psychol 42:53-74;

Mergner T, Rosemeier T (1998) "*Interaction of vestibular, somatosensory and visual signals for postural control and motion perception under terrestrial and microgravity conditions—a conceptual model*" Brain Res Reviews 28:118-135;

Mittelstaedt H (1998) "*Origin and processing of postural information*" Neurosci Biobehav Rev 22:473-478.

The foveal region of the primate retina subtends about 5° of visual angle. As a result of this concentration of photoreceptors (cones), high acuity visual information is available from only about 0.03% of the surrounding environment. With each shift in the direction of gaze, new images fall on the highly specialized region of the retina permitting sequential extraction of high resolution visual information from a much larger portion of the world; Volitional shifts of the line of sight can be accomplished with high velocity, saccadic eye movements. Saccades can greatly increase the range of the visual environment that can be surveyed. However, eye movements are neuromechanically restricted such that when the eyes begin in a central orbital position, the largest movements do not typically exceed ±40 to 45°. To extend these limits without moving the body, animals with mobile heads can redirect the line of sight by simultaneously moving the head and eyes.

Perception of body spatial orientation and eye-head coordination for gaze orientation towards visual targets are different tasks and involve different processing mechanisms. As far as we know, no correlation exists between both behaviours. There is no link between the individual propensity to move the head when changing the direction of the line of sight and the individual preference for visual, vestibular or proprioceptive frame of references for body orientation control.

Thus, according to general knowledge in the field of sensitivity to perception of spatial orientation and to the present invention, measuring the head-eye behaviour of a wearer does not relate to determining a value representing the sensitivity of said wearer to perception of spatial orientation, according to both visual and non visual frame of reference.

One embodiment of the present invention includes thus a step of providing a value, SV, representing the sensitivity of the wearer referred to a scale of sensitivity to perception of spatial orientation, according to both visual and non visual frames of references with the proviso that said value is not provided by measuring the head-eye behaviour of the wearer.

In the frame of the present invention a "design" of a spectacle ophthalmic lens has to be understood as the part of the optical system of said lens which is not determined by the wearer standard prescription parameters consisting of sphere, cylinder, axis and power addition values determined for said wearer.

In addition, in a known manner, the use of the lens by the wearer corresponds to variable directions of observation, i.e. gaze directions, through the lens. Each direction of observation is referenced by two angles, with respect to a horizontal plane and with respect to a vertical plane respectively. A light ray coming from a given direction of observation intersects each face of the lens at two respective points of intersection, and passes through a center of rotation of the eye that is assumed to be fixed. The points of intersection of the light ray with each face of the lens are determined according to the principles of optical refraction. The optical power repartition and astigmatism values of the lens for a given direction then result from the sphere and cylinder values of each face of the lens at the points of intersection of the optical ray and of the value of the refractive index of the intermediate medium as well as its possible gradient.

According to embodiments of the present invention, the calculation or selection of the design for the wearer relates to one eye or both eyes of the wearer.

Spectacle ophthalmic lenses, and particularly progressive lens, are fraught with residual aberrations, mostly unwanted astigmatism and/or unwanted optical power repartition according to gaze direction. Thus, the invention provides for customizing the management of the sensitivity to perception of spatial orientation, according to both visual and non visual frame of reference, of the wearer and thus optimizing the acuity/distortion compromise. In fact, the inventors were able to verify that the impact of residual astigmatism and/or optical power repartition according to gaze direction on vision depends on the sensitivity to perception of spatial orientation, according to both visual and non visual frame of reference.

Spatial orientation is the ability to maintain the body orientation and/or posture in relation with environment (physical space) at rest and during motion.

Spatial orientation relies for example on the use of visual, vestibular (organs of equilibrium located in the inner ear), proprioceptive (receptors located in the skin, muscles, tendons, and joints), auditory, sensory information.

Spatial orientation thus relates to the capacity to assess the physical relationship between the body and the environment, and to deal with modifications in this relationship during movement.

In order to determine the perception of spatial orientation ability of a wearer, one can choose a frame of reference for a sensory information type and measure the sensitivity of the wearer when the frame of reference for said sensory information varies.

One can thus determine for example the sensitivity to visual, or vestibular, or proprioceptive, or auditory information.

Prior knowledge is another frame of reference that can be studied and which relates to the knowledge the wearer already has before they meet new information.

According to examples the proprioceptive sensitivity, which relates to the unconscious perception of movement and spatial orientation arising from stimuli within the body, is measured in tests that measure the subject's ability to detect an externally imposed passive movement, or the ability to reposition a joint or a part of the body to a predetermined position. Error in the detection of the posture of the body relative to real gravity or error in the perception of what the true vertical of the environment is, may be measured so as to quantify the proprioceptive sensitivity.

According to an embodiment of the present invention, providing the value, SV, representing the sensitivity of the wearer referred to a scale of sensitivity to perception of spatial orientation comprises measuring the perception of spatial orientation of the wearer according to the method comprising the steps of:
 a1) measuring the value of a parameter representative of the perception of spatial orientation when the wearer's body is arranged according to a first non visual frame of reference;
 a2) modifying the first non visual frame of reference and thus providing a second non visual frame of reference and measuring the value of the parameter representative of the perception of spatial orientation;
 b1) measuring the value of the parameter representative of the perception of spatial orientation when the wearer's eyes are provided with a first visual frame of reference;
 b2) modifying the first visual frame of reference so as to provide a second visual frame of reference and measuring the value of the parameter representative of the perception of spatial orientation;
 c) combining the measured values of the parameters representative of the perception of spatial orientation of steps a1), a2), b1), b2) so as to obtain the value, SV, representing the sensitivity of the wearer referred to a scale of sensitivity to perception of spatial orientation.

According to the present invention and thanks to measuring the value of a parameter representative of the perception of spatial orientation according both to a non visual frame of reference and to a visual frame of reference and then combining both measured values so as to obtain a value representing the sensitivity of the wearer referred to a scale of sensitivity, one can quantify the perception of spatial orientation of a wearer in complex situations.

According to an embodiment of the present invention, the non visual frame of reference is selected in the list consisting of a proprioceptive frame of reference, a vestibular frame of reference, a non visual prior knowledge frame of reference, an auditory frame of reference.

According to an embodiment of the present invention, the non visual frame of reference is a proprioceptive frame of reference and following embodiments may be implemented and may be combined according to all possible combinations:
 modifying a proprioceptive frame of reference comprises modifying an exocentered spatial mass repartition of the parts of the body of the wearer;
 the variation of the exocentered spatial mass repartition of the parts of the body of the wearer is provided by adding at least a weight to at least a body part of the wearer;
 the part of the body to which at least a weight is attached is chosen in the list consisting of the head, the shoulder(s), part(s) of the trunk such as the dorsal region, the lumbar region;
 the variation of the exocentered spatial mass repartition of the parts of the body of the wearer is provided by inclining the supporting surface of the wearer;
 the variation of the exocentered spatial mass repartition of the parts of the body of the wearer is a variation between two static positions;
 the variation of the exocentered spatial mass repartition of the parts of the body of the wearer is a dynamic variation;
 modifying a proprioceptive frame of reference comprises providing a vibratory stimulation to the muscles and/or the tendons of the wearer.

The invention also relates to a method according to preceding embodiments wherein the variation of the exocentered spatial mass repartition of the parts of the body of the wearer is a variation between two static positions, the visual frames of reference are static visual scenes and a value, SV_Stat, is accordingly determined to represent the static sensitivity of the wearer referred to a scale of sensitivity to perception of spatial orientation.

The invention also relates to a method according to preceding embodiments wherein the variation of the exocentered spatial mass repartition of the parts of the body of the wearer is a dynamic variation, the visual frames of reference are dynamic visual scenes and a value, SV_Dyn, is accordingly determined to represent the dynamic sensitivity of the wearer referred to a scale of sensitivity to perception of spatial orientation.

According to an embodiment of the present invention, the non visual frame of reference is a vestibular frame of reference and where modifying a vestibular frame of reference comprises providing an electrical and/or a caloric stimulation to the ear region of the wearer.

According to an embodiment of the present invention, the non visual frame of reference is a non visual prior frame of reference and where modifying a prior knowledge frame of reference comprises providing verbal instructions to the wearer.

According to an embodiment of the present invention, providing a first visual frame of reference and modifying the first visual frame of reference so as to provide a second visual frame of reference comprises providing a first visual scene and modifying the first visual scene dynamically.

According to another embodiment of the present invention, providing a first visual frame of reference consists in providing a first static visual scene and providing a second visual frame of reference consists in providing a second static visual scene.

According to an embodiment of the present invention, providing a first visual frame of reference and modifying the first visual frame of reference so as to provide a second visual frame of reference comprises providing a first visual scene and tilting and/or shifting the first visual scene.

According to an embodiment of the present invention, the visual frame of reference is provided by projecting a three dimensional virtual visual scene on a screen.

According to an embodiment of the present invention, the three dimensional virtual visual scene comprises lines that are recognizable by the wearer as horizontal or vertical lines.

According to said embodiment the three dimensional virtual visual scene is an architectural or a landscape scene.

According to an embodiment of the present invention, the parameter representative of the perception of spatial orientation is the difference between at least a perceived and an actual vertical line.

According to said embodiment, the measuring method of the parameter representative of the perception of spatial orientation is a Rod and Frame Test. The Rod and Frame Test (RTF) is one of the key measures of the cognitive style construct of field-dependence-independence. During the test, observers view a tilted square frame which takes up most of the visual field, and an adjustable rod which tilts on the same center as the frame. They are asked to adjust the rod to the gravitational vertical, and these adjustments vary greatly (see Oltman P K. *A portable rod-and-frame apparatus*, Percept. Mot. Skills 26:503-6, 1968 [Psychol. Lab., Dept. Psychiat., State Univ. New York Downstate Medical Center, Brooklyn, N.Y.] and also Witkin H A, Goodenough D R & Oltman P K. *Psychological differentiation: current status.* J. Personal. Soc. Psychol. 37:1127-45, 1979).

According to an example, the measured parameter is the deviation error of a rod between the perceived and the actual vertical or horizontal. The measured parameter can also be the deviation error of a rod between the perceived and actual axis of a part of the body, such as the head or the trunk. In order to obtain a mean value and a variance value for the measured parameter, one provides for example on a computer screen a series of rod orientation shifted to the right and to the left from the actual vertical and the wearer has to use the mouse or keys of the keyboard to indicate the perceived spatial orientation. A deviation error is calculated for each rod orientation and the "just noticeable difference" is calculated so as to estimate the variance value and the "point of subjective equality" is calculated so as to estimate the deviation error mean value.

The measuring of the perception of spatial orientation may be implemented according to following embodiments that may be combined:
  the measuring steps of steps a1) and a2) are implemented without providing any visual scene to the wearer;
  the steps a1) and a2) are implemented with the same visual scene provided to the wearer, the steps b1) and b2) are implemented with the same non visual frame of reference provided to the wearer and the combination of measured values of step c) is implemented according to a multisensory integration model; according to an example the multisensory integration model is selected in the list consisting of a Bayesian model, a Maximum Likelihood Estimation (MLE) model, a "winner-take-all" model;
  the steps a2) and b2) are implemented simultaneously; a modification of both visual and non visual frames of reference is thus provided simultaneously;
  both preceding embodiments are implemented and the result of the combination of the measured values of step c) where step a1) and a2) are implemented with the same visual scene and b1) and b2) implemented with the same non visual frame of reference is further compared with the result of the combination of the measured values of step c) when steps a2) and b2) are implemented simultaneously so as to test, and possibly correct, the result of the multisensory integration model;
  a plurality of non visual frames of reference is chosen and the steps a1 and a2 are implemented for each chosen non visual frame of reference; a plurality of non visual frame of reference can then be provided to the wearer and their influence on the perception of spatial orientation can be measured for said wearer;
  steps a2, b2, c) are repeated with a plurality of modified non visual frame of reference for a same type of frame of reference; it is then possible to determine for example perception of spatial orientation threshold, when the amplitude of the modification of frame of reference is progressively increased.

Bayesian probability interprets the concept of probability as "a measure of a state of knowledge". The term "Bayesian" refers to Thomas Bayes (1702-1761) who proved a special case of what is now called Bayes' theorem. Laplace proved a more general version of the theorem and used it to approach problems in celestial mechanics, medical statistics and reliability. Bayesian probability interprets "probability" as "the degree of belief (or strength of belief) an individual has in the truth of a proposition" and is in that respect subjective.

Maximum Likelihood Estimation (MLE) is a popular statistical method used for fitting a mathematical model to some data. The modelling of real world data using estimation by maximum likelihood offers a way of tuning the free parameters of the model to provide a good fit. For a fixed set of data and underlying probability model, maximum likelihood picks the values of the model parameters that make the data "more likely" than any other values of the parameters would make them. Maximum likelihood estimation gives a unique and easy way to determine solution in the case of the normal distribution and many other problems, although in very complex problems this may not be the case. If a uniform prior distribution is assumed over the parameters, the maximum likelihood estimate coincides with the most probable values thereof.

According to an embodiment of the present invention, "combining the measured values of the parameters representative of the perception of spatial orientation of steps a1), a2), a3), a4)" comprises:

c1) calculating a variation index (VI_NV) for the parameter representative of the perception of spatial orientation according to the non visual frame of reference modifications (resulting from steps a1) and a2)) and calculating a variation index (VI_V) for the parameter representative of the perception of spatial orientation according to visual frame of reference modification (resulting from steps b1) and b2));

c2) obtaining the value representing the sensitivity of the wearer by calculating a relative variation between the variation index (VI_V) according to visual frame of reference modification and the variation index (VI_NV) according to non visual frame of reference modification.

According to preceding embodiment, calculating a variation index (VI) according to a frame of reference modification in step c1), consists in calculating the ratio between the amplitude of the variation of the value of the parameter representative of the perception of spatial orientation and the amplitude of the modification of the frame of reference, between a2) and a1) to calculate VI_NV, and between b2) and b1) to calculate VI_V.

According to an embodiment, calculating the relative variation between the variation indexes according to respectively visual and non visual frame of reference modifications, consists in calculating a ratio between VI_V and VI_NV.

According to an embodiment of the present invention, the scale of sensitivity to perception of spatial orientation is a numeral scale where the higher is the value representing the sensitivity of the wearer, the higher is the visual dependence compared to the non visual dependence according to the non visual frame of reference of steps a1), a2).

According to an example, the calculation of the relative variation between the variation indexes according to respectively visual and non visual frame of reference modifications comprises a normalisation step so as the scale of sensitivity to perception of spatial orientations varies from 0 to 1, where a 0 value corresponds to no visual dependence and 1 corresponds to a total visual dependence.

It has to be enlightened that the present invention is not limited to the exemplified scale of sensitivity and that scales of sensitivity using a non numeral scale can be used (such as letters, for example A, B, C, D, E, linked to a sensitivity level). Furthermore, the direction of the variation is not limited from low, respectively high, sensitivity value corresponding to low, respectively high, visual dependence but can be for example opposite.

According to an example the value SV representing the sensitivity of the wearer referred to a scale of sensitivity to perception of spatial orientation is calculated according to following equation (1) where one non visual frame of reference influence is tested:

$$SV = \frac{VI\_V/VI\_NV}{1 + (VI\_V/VI\_NV)} \quad (1)$$

Corresponding scale of sensitivity varies from 0 to 1, and when SV is low, respectively high, the wearer has a low, respectively high, visual dependence.

According to another example, where a plurality of non visual frame of reference is tested the value SV representing the sensitivity of the wearer is calculated according to following equation (2):

$$SV = \frac{VI\_V/(w1 \cdot VI\_NV1 + \ldots + wn \cdot VI\_NVn)}{1 + (VI\_V/(w1 \cdot VI\_NV1 + \ldots + wn \cdot VI\_NVn))} \quad (2)$$

where:

n is the number of non visual frames of reference that are tested;

VI_NV1 to VI_NVn are the variation indexes according to the different tested non visual frames of reference;

w1 to wn are weight values used to take into account the importance of each of the non visual frame of reference; according to an example, each weight values are equal to 1;

According to an example n=4 and VI_NV1, VI_NV2, VI_NV3, VI_NV4 corresponds to the variation index according to respectively a proprioceptive, a vestibular, a non visual prior knowledge, an auditory frame of reference.

According to an embodiment of the present invention the scale of sensitivity to perception of spatial orientation is a numeral scale where the higher is the value, SV, representing the sensitivity of the wearer, the higher is the visual dependence compared to the non visual dependence according to the non visual frame of reference.

According to an embodiment of the present invention the spectacle ophthalmic lens is a spectacle progressive addition lens and wherein the calculation or the selection of the design for the wearer is performed according to a characteristic relating to softness/harness feature of the progressive addition lens.

According to preceding embodiment the higher is the value, SV, representing the sensitivity of the wearer, the softer is the design of the spectacle progressive addition lens.

According to preceding embodiment, where SV_Stat and SV_Dyn are determined, the addition of the spectacle progressive addition lens is placed on the front face (FF) and/or on the back face (BF) of the lens and the contribution to the lens addition of the front face of the lens increases when the ratio SV_Stat/(SV_Stat+SV_Dyn) increases.

In the frame of the present invention, a "lens hardness parameter" has to be understood as a parameter suitable for characterizing ophthalmic lens peripheral aberrations management. Said aberrations management relates to the vision fields apertures in the far and near vision zones and thus to the variation degree of aberration along the ophthalmic lens periphery. According to non limiting examples, a lens hardness parameter is maximum astigmatism gradient on a lens surface, or maximum dioptric power gradient on a lens surface, or a combination thereof.

Progressive lens designs are broadly categorised as either "hard" type designs or "soft" type designs based on the distribution of power and astigmatism.

Hard lens designs concentrate the aberrations into smaller regions of the lens surface, thereby expanding the areas of clear vision at the expense of elevating the gradients and overall magnitude of unwanted cylindrical power in the periphery.

Soft lens designs spread the aberrations across larger regions of the lens surface, thereby reducing the gradients and overall magnitude of unwanted cylindrical power at the expense of narrowing the areas of clear vision.

According to examples, soft lens designs use a longer progressive corridor length with a relatively slow progression of addition power, while hard lens designs use a shorter corridor length with a relatively rapid progression of addition power.

According to an embodiment of the present invention, the method further comprises providing the eye-head coefficient, EHC, for the wearer and wherein the addition of the spectacle progressive addition lens is placed on the front face (FF) and/or on the backface (BF) of the lens and the contribution to the lens addition of the front face of the lens decreases when the eye-head coefficient, EHC, increases.

In the frame of the present invention, "Eye-head coefficient", EHC, is a coefficient suitable to characterize the relative amplitudes of movements respectively of the eyes and of the head of a wearer when the gaze direction of the wearer is changing. An eye-head coefficient can be measured for a wearer thanks to an "eye/head" movement coordination test.

According to an embodiment, the EHC is a function of angular deviation ($\alpha_T$) of the wearer's head divided by an angular eccentricity (E) of a target which the wearer is looking at. Said EHC is equal to 1 for a wearer who has only turned his head when looking at the target and equal to 0 for a wearer who has only turned his eyes when looking at the target.

Another aspect of the invention relates to a method for manufacturing a spectacle ophthalmic lens for a wearer, the method comprising the following steps:

aa) providing a value, SV, representing the sensitivity of the wearer referred to a scale of sensitivity to perception of spatial orientation, according to visual and non visual frames of reference;

bb) calculating a design of the spectacle ophthalmic lens or selecting a design in a spectacle ophthalmic lens design data base, for example thanks to a method implemented by computer means, by adapting the management of residual astigmatism and/or optical power repartition according to gaze directions based on the value, SV, representing the sensitivity of the wearer referred to a scale of sensitivity to perception of spatial orientation;

cc) providing a lens substrate;

dd) manufacturing the spectacle ophthalmic lens according to the optical system (OS) corresponding to the calculated or selected design in step bb).

According to different embodiments, said method for manufacturing incorporates the previously described features and the different embodiments of the preceding method for providing a spectacle ophthalmic lens to a wearer.

The method according to the invention can also be used to optimize the selection of an already existing lens design. In particular, it is possible to either use or not use a function allowing for a better fit with a prescribed correction in the whole of the visual field, or a function taking into account assembly parameters and mode of wear, depending on the value, SV, representing the sensitivity of the wearer referred to a scale of sensitivity to perception of spatial orientation, according to both visual and non visual frame of reference.

Another aspect of the invention relates to a computer program product comprising one or more stored sequence of instruction that is accessible to a processor and which, when executed by the processor, causes the processor to carry out at least one of the steps of the different embodiments of the preceding methods.

Another aspect of the invention relates to a computer-readable medium carrying one or more sequences of instructions of the preceding computer program product.

Unless specifically stated otherwise, as apparent from the following discussions, it is appreciated that throughout the specification discussions utilizing terms such as "computing", "calculating" "generating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMS) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

The features of the present invention, as well as the invention itself, both as to its structure and its operation, will be best understood from the accompanying non limiting drawings and examples, taken in conjunction with the accompanying description, in which.

Skilled artisans appreciate that elements in the figures are illustrated for simplicity and clarity and have not necessarily been drawn to scale. For example, the dimension of some of the elements in the figures may have been exaggerated relative to other elements to help improve the understanding of the embodiments of the present invention. Identical numeral references in the figures refer to the same element.

DESCRIPTION OF PREFERRED EMBODIMENTS

Figure 1:
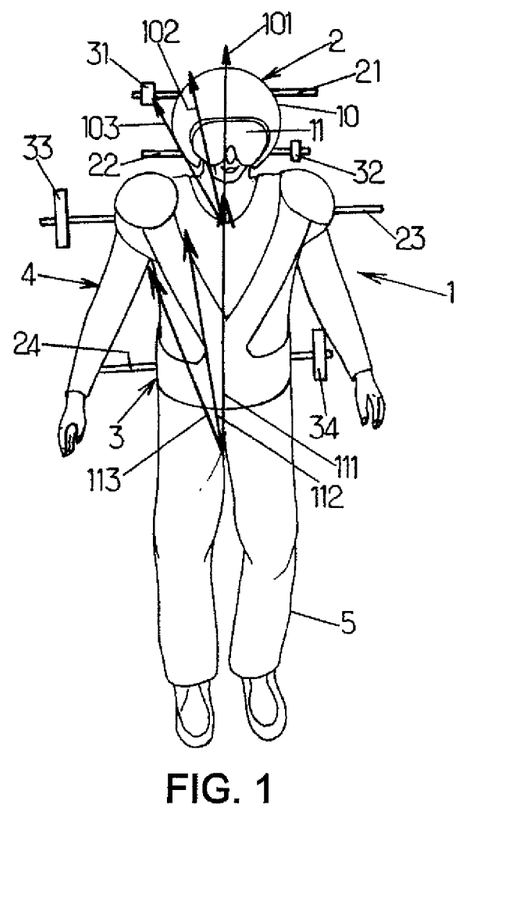
FIG. 1 shows an example of means to modify the proprioceptive frame of reference of a wearer.

FIG. 1 shows a standing wearer 1 equipped with a plurality of mass holding means 21, 22, 23, 24 attached to different parts of the body of the wearer. Mass holding means 21 and 22 are attached to the head 2 of the wearer thanks to a virtual reality helmet 10. Mass holding means 23 and 24 are attached to the upper part and the lower part of the trunk 3 of the wearer.

Each mass holding means 21, 22, 23, 24 comprises a bar which is suitable to receive weights, respectively weights 31, 32, 33, 34; said weights are movable along said bars and can be fixed in a desired position.

The virtual reality helmet 10 comprises a part surrounding the head 2 on which bars are fixed and a screen 11 on which virtual images can be projected.

According to an embodiment of the present invention where the non visual frame of reference to be tested is a proprioceptive frame of reference, the exocentered spatial mass repartition of the parts of the body of the wearer may be modified according to three types of axis:

geometrical axis 101, 111, which relates to the distribution of the mass of the parts of the body, thus to the articular geometry of said body;

mass center axis 102, 112, which relates to first moment linked to the rotation axis passing through the mass center of the distribution of mass of the body;

inertia axis (called e3), 103, 113, which relates to second moment linked to inertial rotation axis of the distribution of the mass of the body and thus relates to dynamic components.

When only the head moves, axis 101, 102, 103 have to be considered.

When the whole body moves, axis 111, 112, 113 have to be considered and relates to the head 2, trunk 3 and legs 5 system.

In order to modify the proprioceptive frame of reference of the head and to let vary the spatial position of axis 101, 102, 103, the positions of weights 31 and 32 are modified.

In order to modify the proprioceptive frame of reference of the whole body and to let vary the spatial position of axis 111, 112, 113, the positions of weights 31, 32, 33 and 34 are modified.

Modification of the proprioceptive frame of reference can also results from moving a limb, such as an arm 4 or a leg 5.

Examples of modifications of a proprioceptive frame of reference and their relationship to the perception of a part of a body are disclosed in following publications:

"*Perception of limb orientation in the vertical plane depends on center of mass rather than inertial eigenvectors*"—Rolf van de Langenberg Idsart Kingma; Peter J. Beek—*Exp. Brain Res* (2007) 180:595-607;

"*Differential exploitation of the inertia tensor in multi-joint arm reaching*"—Delphine Bernardin; Brice Isableu; Paul Fourcade; Benoit G. Bardy—*Exp Brain Res* (2005) 167: 487-495).

Examples of methods for measuring the value of a parameter representative of the perception of spatial orientation are given in said publications, such as measuring the difference in limbs orientation or when pointing at a target according to different exocentered spatial mass repartitions of the parts of the body.

Figure 2:
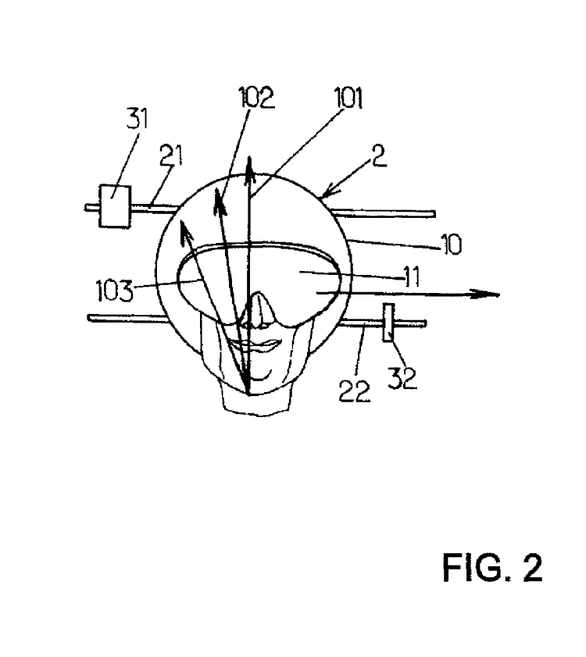
FIG. 2 shows an example of combining proprioceptive and visual frames of reference modifications.

According to an embodiment of the present invention, and as illustrated in FIG. 2 a moving visual scene is provided to the wearer on the screen 11 of the virtual reality helmet 10. The horizontal arrow on FIG. 2 indicates the view on the helmet which is a continuously moving architectural scene from image (a) to image (b) and reverse. Such an architectural scene comprises lines that are recognizable by the wearer as horizontal and vertical lines.

The wearer is then asked to determine the perceived vertical or horizontal line.

Figure 3:
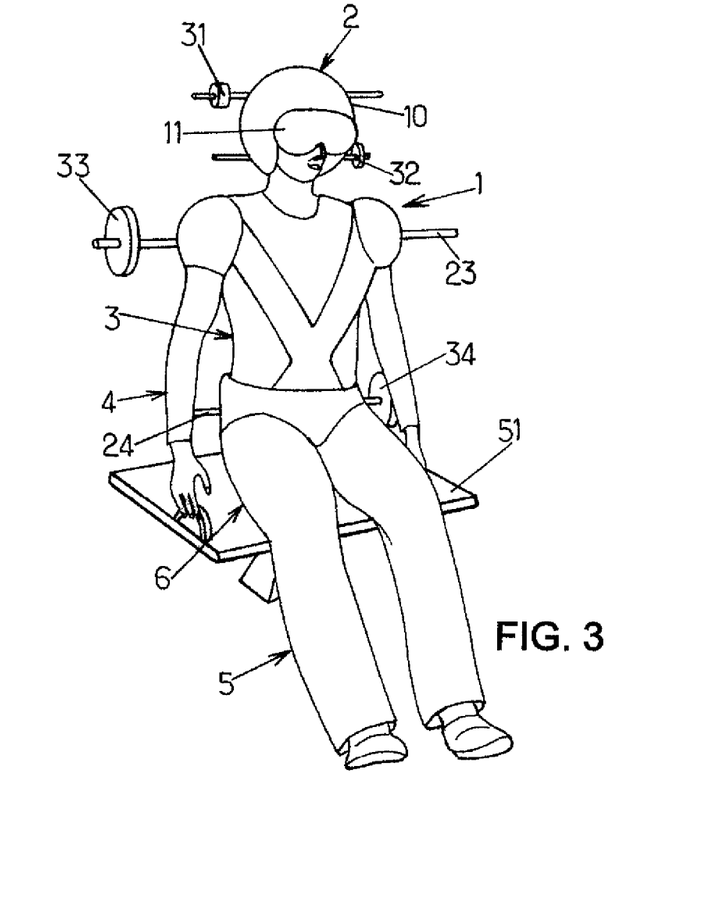
FIGS. 3 and 4 show other examples of means to modify the proprioceptive frame of reference of a wearer.

According to another embodiment illustrated on FIG. 3, the wearer is sitting and his buttock 6 is placed on a moving board 51 so as to modify the proprioceptive frame of reference corresponding to the gluteal support.

Figure 4:
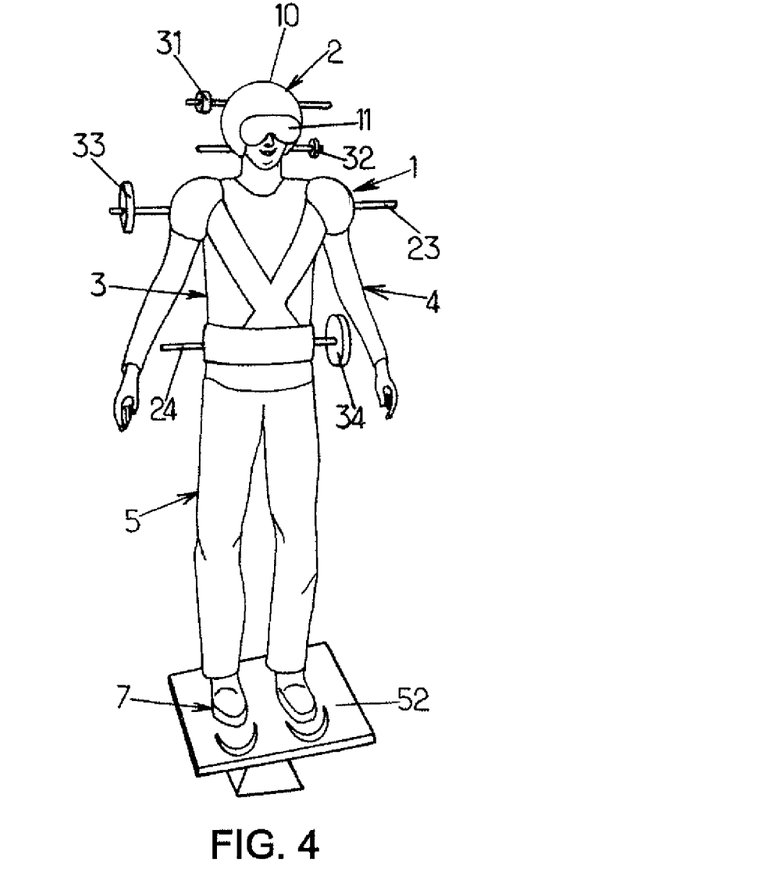

According to the embodiment illustrated on FIG. 4, the wearer is standing and his feet 7 are placed on a moving board 52 so as to modify the proprioceptive frame of reference corresponding to the feet support.

The moving board 51, 52 may be mechanized so as to precisely control its position variations.

The FIGS. 5*a* to *d* show different configurations of a virtual reality helmet 10 according to the present invention where the weights 41 to 48 are placed along the bars 21 and 22 in different positions in order to test the sensitivity of the wearer to different variations of the proprioceptive frame of reference, namely according to different rotation axes of the egocentric frame of reference.

Figure 5A:
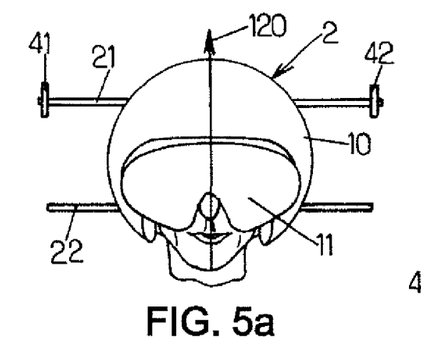
FIGS. 5a to d show different configurations of a virtual reality helmet according to the present invention.

In FIG. 5*a*, the weights 41 and 42 are equal and placed symmetrically to the geometrical axis on the same bar 21. The direction 120 thus corresponds to geometrical axis, to the mass center axis and to the inertia e3 axis. According to this embodiment, these three axes are merged together.

Figure 5B:
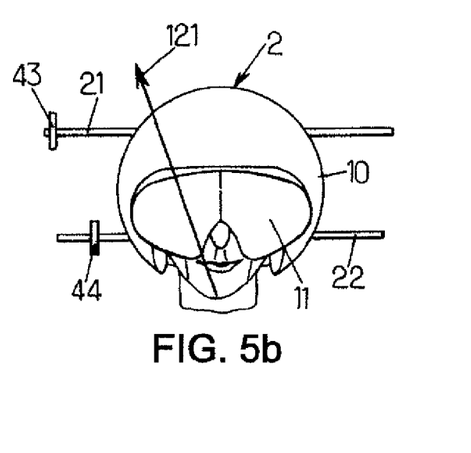

In FIG. 5*b*, both weights 43 and 44 are equal and placed at the right side of the head, respectively on the upper bar 21 and the lower bar 22. According to this embodiment, the direction 121 corresponds both to the mass center axis and to the inertia e3 axis. According to this embodiment, these two axes are merged together and the geometrical axis remains as represented in FIG. 5*a*.

Figure 5C:
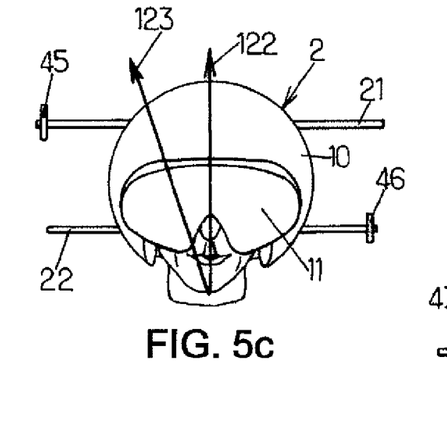

In FIG. 5*c*, the weights 45 and 46 are equal and placed at the same distance of the geometrical axis, but weight 45 is placed on the upper bar 21 and weight 46 is placed on the lower bar 22. Direction 122 corresponds to the mass center axis and direction 123 corresponds to the inertia e3 axis. According to this embodiment, the geometrical axis and the mass center axis are merged together.

Figure 5D:
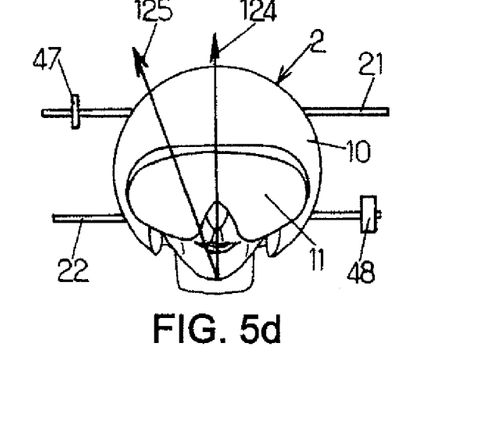

In FIG. 5*d*, the weight 48 is significantly heavier than weight 47 and the weight positions according to bars 21 and 22 are similar to the ones of FIG. 5*c*. Direction 124 corresponds to the inertia e3 axis and direction 125 corresponds to the mass center axis. According to this embodiment, the geometrical axis and the inertia e3 axis are merged together.

Each of the FIGS. 1, 3, 4 and 5*a* to *d* embodiments corresponds to testing different main characteristics of the body and/or of the head proprioceptive frame of reference. Combining said variations of the proprioceptive frame of reference with variations of the visual frame of reference makes possible to determine the sensitivity of the wearer to combined visual and non visual frame of reference variations. According to the present invention, said sensitivity is referred to a scale of sensitivity to perception of spatial orientation. It is then possible to measure the perception of spatial orientation of a wearer in complex visual/non visual situations that can be taken into account to customize a spectacle ophthalmic lens for a wearer.

Figure 6A:
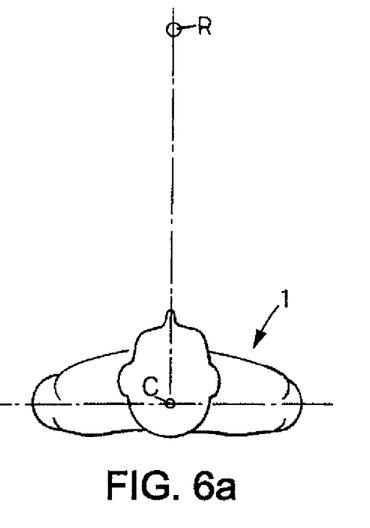
FIGS. 6a and b illustrate a principle of measurement of eyes and head movement.
Figure 6B:
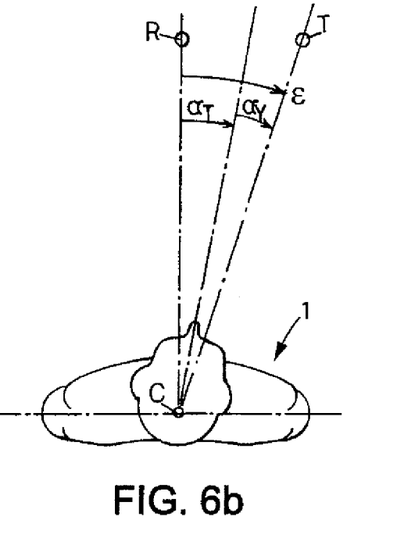

FIGS. 6a and *b* illustrate a principle of measurement of eyes and head movements for a spectacle lens wearer 1 when looking at a first target R situated in front of the wearer. The wearer firstly looks at said target R as shown on FIG. 6a and is then asked to look at a test target T without moving his shoulders as shown on FIG. 6b. The angular shift between both targets is called the eccentricity and referred as E. $\alpha_T$ is the head angular shift for the wearer 80 and $\alpha\gamma$ is his eyes angular shift whereas $E=\alpha_T+\alpha\gamma$. An eye-head coefficient EHC can be defined as a growing function of the ratio between $\alpha_T$ and E. According to an example $EHC=\alpha_T/E$. Details of said eyes and head measurement method are given in the patent publication WO 2008/104695 (namely on pages 5 and 6 of said document) which is hereby incorporated by reference.

The EHC determined for a wearer can then be used as a parameter used to calculate the DP2 design parameter disclosed above.

Figure 7:
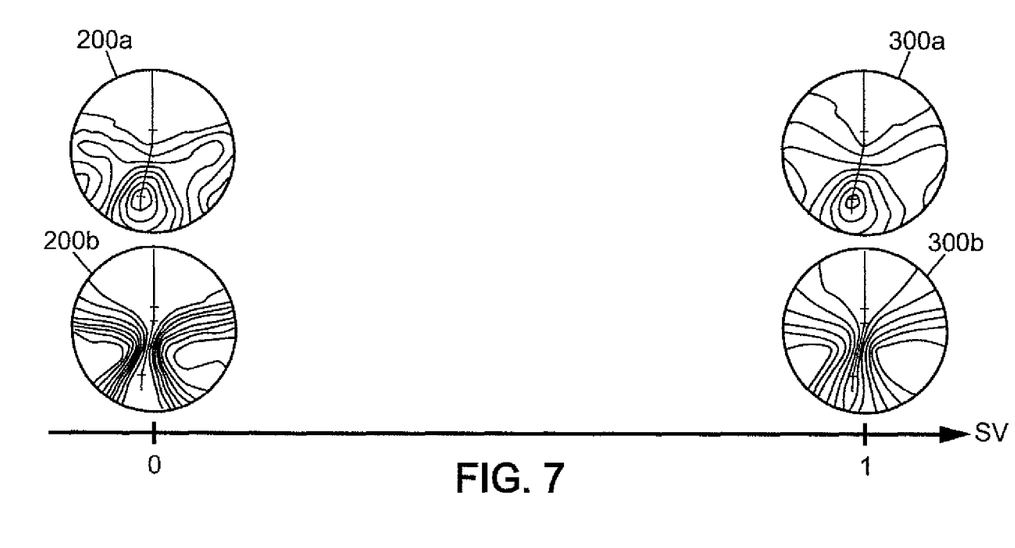
FIG. 7 illustrates a selection chart according to the present invention for a spectacle ophthalmic lens design according to SV parameter.

FIG. 7 illustrates an example of selection chart for customizing progressive addition ophthalmic lenses (PAL) for a wearer according to the present invention.

The abscissa corresponds to the variation from 0 to 1 of the parameter SV as defined according to here above mentioned equation (1).

The inventors have demonstrated that the visual comfort of a wearer is improved when wearing a hard PAL design if his SV value is low (close to 0). Accordingly, one can offer him a hard PAL design such as exemplified on the PAL represented in FIG. 7, above the abscissa value SV=0. Lines on map 200b are iso-astigmatism curves and lines on map 200a are iso-dioptric power curves of said hard design PAL.

The visual comfort of a wearer is improved when wearing a soft PAL design if his SV value is high (close to 1). Accordingly, one can offer him a soft PAL design such as exemplified on the PAL represented in FIG. 7, above the abscissa value SV=1. Lines on map 300b are iso-astigmatism curves and lines on map 300a are iso-dioptric power curves of said soft design PAL.

The design of the customized lens for a wearer is progressively shifted from the hard PAL design (200a, 200b) when SV=0 to the soft PAL design (300a, 300b) when SV=1 according to a proportionality factor related to the SV value for the wearer. According to this embodiment, the PAL design is "neutral" (medium hard/medium soft) when SV=0.5.

Figure 8:
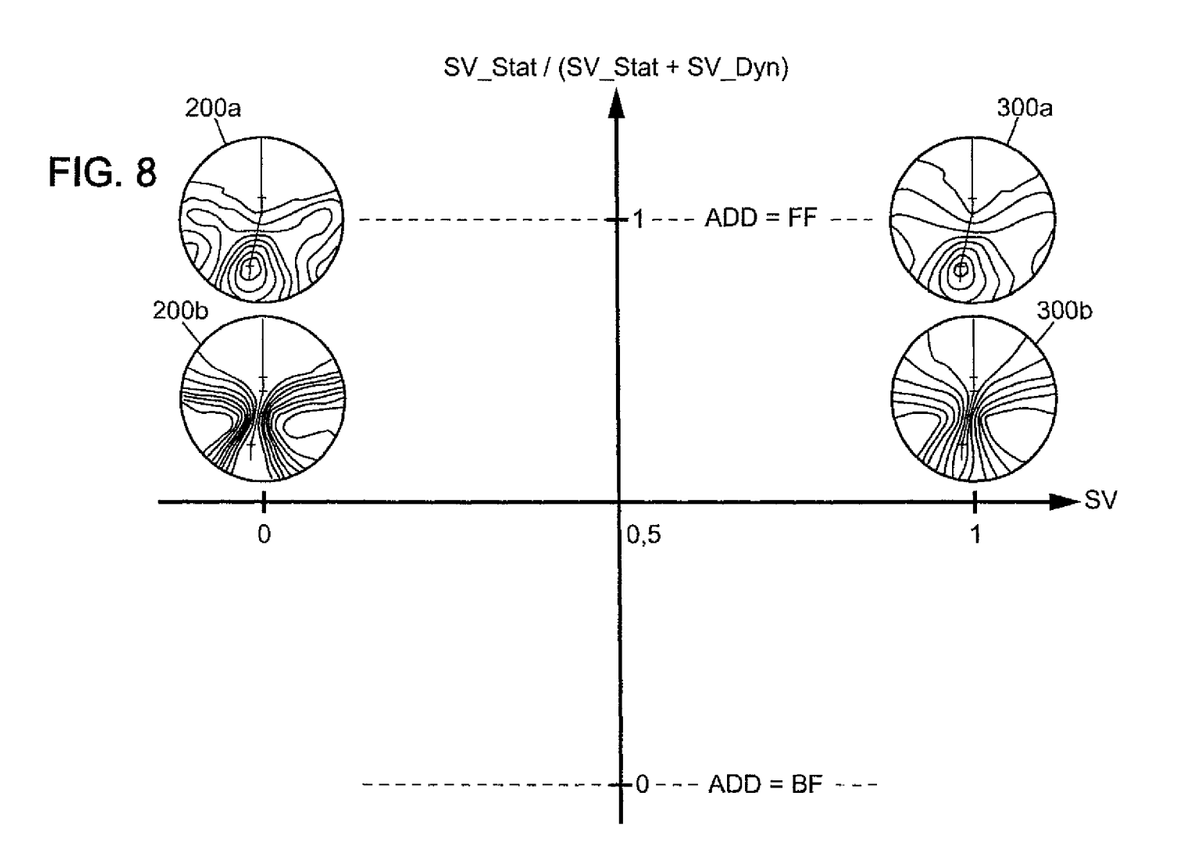
FIG. 8 illustrates a selection chart according to the present invention for a spectacle ophthalmic lens design according to SV parameter and according to the static/dynamic sensitivity of the wearer.

FIG. 8 illustrates an example of selection chart for customizing progressive addition ophthalmic lenses (PAL) for a wearer according to the present invention where data of FIG. 7 are reported. A complementary factor is taken into account, where the static/dynamic sensitivity of the wearer is considered.

According to said example, the parameter SV_Stat/(SV_Stat+SV_Dyn) is determined for the wearer as previously disclosed. Said parameter varies from 0 to 1, where a 0 value corresponds to a wearer which sensitivity to perception of spatial orientation is purely dynamic and a 1 value corresponds to a wearer which sensitivity to perception of spatial orientation is purely static.

The inventors have demonstrated that the visual comfort of a wearer is furthermore improved when selecting a PAL design as illustrated on FIG. 7 according to the SV value and when the addition (corresponding to the intermediate and near vision zones of the PAL) is placed on the front face (written on FIG. 8 as "ADD=FF") if SV_Stat/(SV_Stat+SV_Dyn)=1 and when the addition is placed on the back face (written on FIG. 8 as "ADD=BF") if SV_Stat/(SV_Stat+SV_Dyn)=0. According to this example, the contribution of the front/back faces is progressively shifted from 100% on the front face, FF, when SV_Stat/(SV_Stat+SV_Dyn)=1, up to 100% on the back face, BF, when SV_Stat/(SV_Stat+SV_Dyn)=0 depending on the SV_Stat/(SV_Stat+SV_Dyn) value for the wearer.

Figure 9:
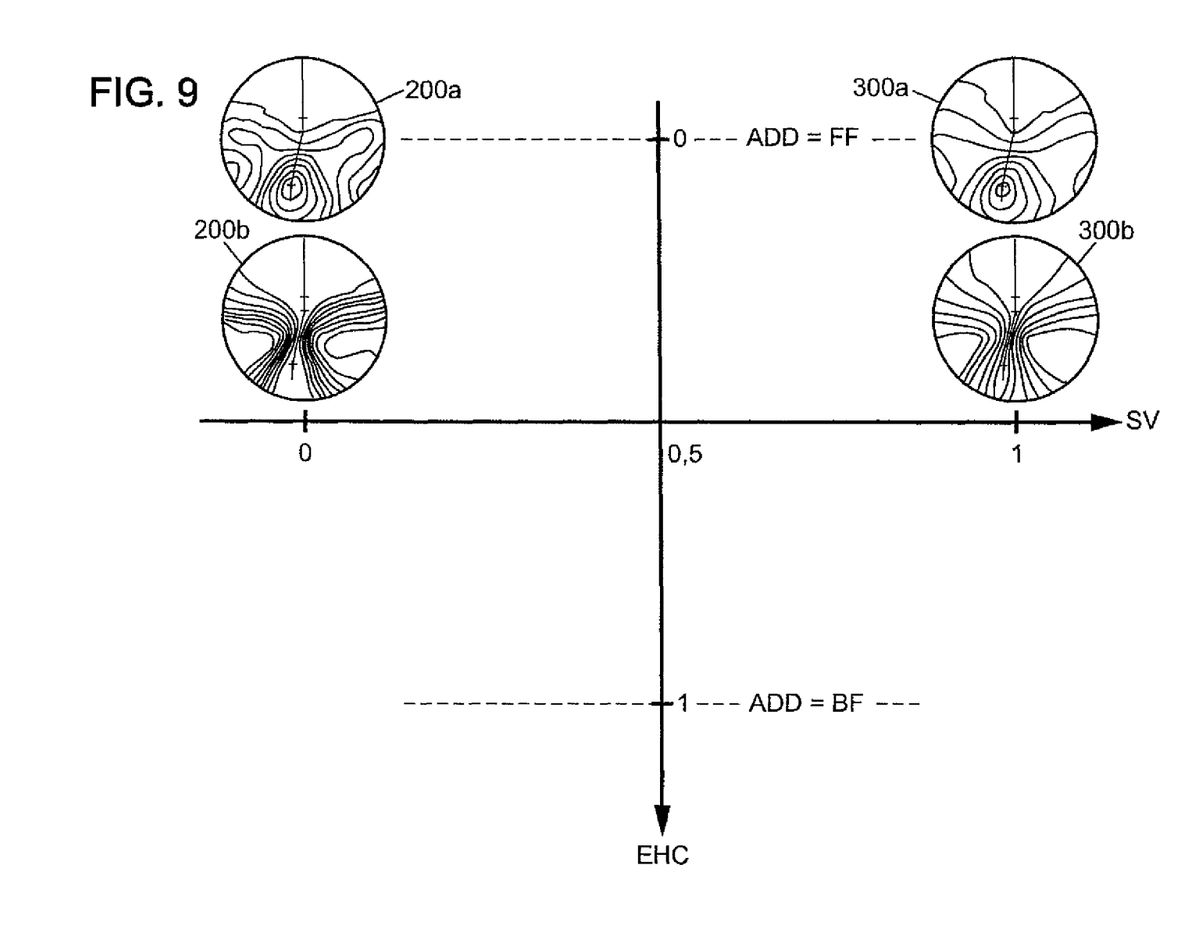
FIG. 9 illustrates a selection chart according to the present invention for a spectacle ophthalmic lens design according to SV parameter and according to the eye-head coefficient for a wearer.

FIG. 9 illustrates an example of selection chart for customizing progressive addition ophthalmic lenses (PAL) for a wearer according to the present invention where data of FIG. 7 are reported. A complementary factor is taken into account, where the eyes-head coefficient, EHC, of the wearer is considered.

A parameter EHC is determined for the wearer as previously disclosed.

The inventors have demonstrated that the visual comfort of a wearer is furthermore improved when selecting a PAL design as illustrated on FIG. 7 according to the SV value and when the addition (corresponding to the intermediate and near vision zones of the PAL) is placed on the front face (written on FIG. 9 as "ADD=FF") if EHC=0 and when the addition is placed on the back face (written on FIG. 9 as "ADD=BF") if EHC=1. According to this example, the contribution of the front/back faces is progressively shifted from 100% on the front face, FF, when EHC=0, up to 100% on the back face, BF, when EHC=1 depending on the EHC value for the wearer.

According to an embodiment of the present invention, both static/dynamic sensitivity, SV_Stat/(SV_Stat+SV_Dyn), and the eyes-head coefficient, EHC, of the wearer are determined. In order to select a customized PAL for the wearer, one can define a combined customization parameter, CCP, according to following equation (3):

$$CCP=[1-EHC+SV\_Stat/(SV\_Stat+SV\_Dyn)]/2$$

The inventors have demonstrated that the visual comfort of a wearer is furthermore improved when selecting a PAL design as illustrated on FIG. 7 according to the CCP value and when the addition (corresponding to the intermediate and near vision zones of the PAL) is placed on the front face, FF, if CCP=1 and when the addition is placed on the back face, BF, if CCP=0. According to this example, the contribution of the front/back faces is progressively shifted from 100% on the front face, FF, when CCP=1, up to 100% on the back face, BF, when CCP=0 depending on the CCP value for the wearer.

According to an embodiment of the present invention, the design of the spectacle ophthalmic lens for a wearer is selected among a plurality of spectacle ophthalmic lens designs according to the present invention and the optical system of the lens for the wearer is obtained by combining the chosen design and the prescription data for the wearer.

According to another embodiment of the present invention, a design is calculated for a wearer by adapting the management of residual astigmatism and/or optical power repartition according to gaze direction based on the value, SV, representing the sensitivity of the wearer referred to a scale of sensitivity to perception of spatial orientation, according to both visual and non visual frame of reference.

Said design calculation may be implemented according to design calculation methods known from a man skilled in the art where a calculation parameter is related to the value, SV, representing the sensitivity of the wearer referred to a scale of sensitivity to perception of spatial orientation, according to both visual and non visual frame of reference of the wearer.

According to a design calculation method suitable for the present invention, a first design is selected and then modified in order to take into account said value, SV, representing the sensitivity of the wearer referred to a scale of sensitivity to perception of spatial orientation, according to both visual and non visual frame of reference. Optimization methods may be implemented where an optimization parameter is the value, SV, representing the sensitivity of the wearer referred to a scale of sensitivity to perception of spatial orientation, according to both visual and non visual frame of reference.

According to an embodiment of the present invention, where a complementary factor(s) is(are) taken into account, the method for manufacturing a spectacle ophthalmic lens for a wearer can be implemented thanks to the method described in the International Patent Application numbered PCT/FR2008/051618, filed on Sep. 11, 2008, in the name of ESSILOR INTERNATIONAL (Compagnie Générale d'Optique), where the value of "gain G qui a été calculée pour le porteur" (the gain factor G, which has been calculated for a wearer) would be equal to following parameters:

the complementary factor is the static/dynamic sensitivity of the wearer, SV_Stat/(SV_Stat+SV_Dyn), and the gain factor G is:

$$G=1-SV\_Stat/(SV\_Stat+SV\_Dyn);$$

the complementary factor is the eyes-head coefficient of the wearer, EHC, and the gain factor G is G=EHC;

the complementary factors are the static/dynamic sensitivity of the wearer, SV_Stat/(SV_Stat+SV_Dyn) and the eyes-head coefficient, EHC, and the gain factor G is G=1−CCP.

The invention has been described above with the aid of embodiments without limitation of the general inventive concept, in particular numerous calculation and/or manufacturing methods known from the man skilled in the art could be used in order to adapt the management of residual astigmatism and/or optical power repartition according to gaze direction according to the present invention.

The invention has been described above with the aid of embodiments without limitation of the general inventive concept. In particular the present invention provides a method for providing a spectacle ophthalmic lens according to the perception of spatial orientation in complex situations not limited to visual/proprioceptive frames of reference modifications, but also to numerous visual/non visual frames of reference modifications. Furthermore, a plurality of non visual frames of reference may be modified step by step or simultaneously.

The invention claimed is:

1. A method implemented by a computer for providing a spectacle ophthalmic lens to a wearer, the method comprising the following steps:
providing a value, SV, representing a sensitivity of the wearer referred to a scale of sensitivity to perception of spatial orientation, according to both visual and non visual frames of reference; and
calculating a design of the spectacle ophthalmic lens or selecting a design in a spectacle ophthalmic lens design data base by adapting a management of residual astigmatism and/or optical power repartition according to gaze direction based on the value, SV, representing the sensitivity of the wearer referred to a scale of sensitivity to perception of spatial orientation,
wherein providing the value, SV, representing the sensitivity of the wearer referred to a scale of sensitivity to perception of spatial orientation comprises measuring the perception of spatial orientation of the wearer, comprises:
a1) measuring the value of a parameter representative of the perception of spatial orientation when the wearer's body is arranged according to a first non visual frame of reference;
a2) modifying the first non visual frame of reference and thus providing a second non visual frame of reference and measuring the value of the parameter representative of the perception of spatial orientation;
b1) measuring the value of the parameter representative of the perception of spatial orientation when the wearer's eyes are provided with a first visual frame of reference;
b2) modifying the first visual frame of reference so as to provide a second visual frame of reference and measuring the value of the parameter representative of the perception of spatial orientation; and
c) combining the measured values of the parameters representative of the perception of spatial orientation of steps a1), a2), b1), b2) so as to obtain the value, SV, representing the sensitivity of the wearer referred to a scale of sensitivity to perception of spatial orientation.

2. The method of claim 1, wherein the non visual frame of reference is selected in the list consisting of a proprioceptive frame of reference, a vestibular frame of reference, a non visual prior knowledge frame of reference, an auditory frame of reference.

3. The method of claim 2, wherein the non visual frame of reference is a proprioceptive frame of reference and where modifying a proprioceptive frame of reference comprises modifying an exocentered spatial mass repartition of the parts of the body of the wearer.

4. The method of claim 3, wherein the variation of the exocentered spatial mass repartition of the parts of the body of the wearer is a variation between two static positions, the visual frames of reference are static visual scenes and a value, SV_Stat, is accordingly determined to represent the static sensitivity of the wearer referred to a scale of sensitivity to perception of spatial orientation.

5. The method according to claim 4, wherein the variation of the exocentered spatial mass reparation of the parts of the body of the wearer is a dynamic variation, the visual frames of reference are dynamic visual scenes and a value, SV_Dyn, is accordingly determined to represent the dynamic sensitivity of the wearer referred to a scale of sensitivity to perception of spatial orientation, wherein the scale of sensitivity to perception of spatial orientation is a numeral scale where the higher is the value, SV, representing the sensitivity of the wearer, the higher is the visual dependence compared to the non visual dependence according to the non visual frame of reference, where the spectacle ophthalmic lens is a spectacle progressive addition lens and wherein the calculation or the selection of the design for the wearer is performed according to a characteristic relating to softness/harness feature of the progressive addition lens and wherein the higher is the value, SV, representing the sensitivity of the wearer, the softer is the design of the spectacle progressive addition lens and wherein the addition of the spectacle progressive addition lens is placed on the front face (FF) and/or on the back face (BF) of the lens and the contribution to the lens addition of the front face of the lens increases when a ratio SV_Stat/(SV_Stat+SV_Dyn) increases.

6. The method of claim 3, wherein the variation of the exocentered spatial mass reparation of the parts of the body of the wearer is a dynamic variation, the visual frames of reference are dynamic visual scenes and a value, SV_Dyn, is accordingly determined to represent the dynamic sensitivity of the wearer referred to a scale of sensitivity to perception of spatial orientation.

7. The method of claim 1, wherein the visual frame of reference is provided by projecting a three dimensional virtual visual scene on a screen.

8. The method according to claim 1, wherein the scale of sensitivity to perception of spatial orientation is a numeral scale where the higher is the value, SV, representing the sensitivity of the wearer, the higher is the visual dependence compared to the non visual dependence according to the non visual frame of reference.

9. The method according to claim 8, where the spectacle ophthalmic lens is a spectacle progressive addition lens and wherein the calculation or the selection of the design for the wearer is performed according to a characteristic relating to softness/harness feature of the progressive addition lens and wherein the higher is the value, SV, representing the sensitivity of the wearer, the softer is the design of the spectacle progressive addition lens.

10. The method according to claim 9, further comprising providing the eye-head coefficient, EHC, for the wearer and wherein the addition of the spectacle progressive addition lens is placed on the front face (FF) and/or on the backface (BF) of the lens and the contribution to the lens addition of the front face of the lens decreases when the eye-head coefficient, EHC, increases.

11. The method according to claim 1, where the spectacle ophthalmic lens is a spectacle progressive addition lens and wherein the calculation or the selection of the design for the wearer is performed according to a characteristic relating to softness/harness feature of the progressive addition lens.

12. A computer program product comprising one or more stored sequence of instruction that is accessible to a processor and which, when executed by the processor, causes the processor to carry out the steps of claim 1.

13. A computer-readable device carrying one or more sequences of instructions of the computer program product of claim 1.

14. A method for manufacturing a spectacle ophthalmic lens for a wearer, the method comprising the following steps:

aa) providing a value, SV, representing a sensitivity of the wearer referred to a scale of sensitivity to perception of spatial orientation, according to visual and non visual frames of reference;
bb) calculating a design of the spectacle ophthalmic lens or selecting a design in a spectacle ophthalmic lens design data base by adapting the management of residual astigmatism and/or optical power reparation according to gaze direction based on the value, SV, representing the sensitivity of the wearer referred to a scale of sensitivity to perception of spatial orientation;
cc) providing a lens substrate;
dd) manufacturing the spectacle ophthalmic lens according to the optical system (OS) corresponding to the calculated or selected design in step bb),
wherein providing the value, SV, representing the sensitivity of the wearer referred to a scale of sensitivity to perception of spatial orientation comprises measuring the perception of spatial orientation of the wearer comprises:
a1) measuring the value of a parameter representative of the perception of spatial orientation when the wearer's body is arranged according to a first non visual frame of reference;
a2) modifying the first non visual frame of reference and thus providing a second non visual frame of reference and measuring the value of the parameter representative of the perception of spatial orientation;
b1) measuring the value of the parameter representative of the perception of spatial orientation when the wearer's eyes are provided with a first visual frame of reference;
b2) modifying the first visual frame of reference so as to provide a second visual frame of reference and measuring the value of the parameter representative of the perception of spatial orientation; and
c) combining the measured values of the parameters representative of the perception of spatial orientation of steps a1), a2), b1), b2) so as to obtain the value, SV, representing the sensitivity of the wearer referred to a scale of sensitivity to perception of spatial orientation.

* * * * *